United States Patent [19]

Robbins

[11] Patent Number: 4,609,448
[45] Date of Patent: Sep. 2, 1986

[54] CATHODIC PROTECTION MONITOR SYSTEM FOR SUBMERGED STRUCTURES

[75] Inventor: Gregory K. Robbins, Mandeveille, La.

[73] Assignee: Texaco Inc., White Plains, N.Y.

[21] Appl. No.: 685,645

[22] Filed: Dec. 24, 1984

[51] Int. Cl.$^4$ .................... C23F 13/00; G01N 27/30
[52] U.S. Cl. .................... 204/197; 204/286; 204/297 R; 204/404; 204/435
[58] Field of Search ............... 204/147, 148, 196, 197, 204/286, 297 R, 1 T, 1 C, 404, 400, 435

[56] References Cited

U.S. PATENT DOCUMENTS

| | | | |
|---|---|---|---|
| 4,056,446 | 11/1977 | Vennett | 204/196 |
| 4,089,767 | 5/1978 | Sabins | 204/197 |
| 4,251,343 | 2/1981 | Peterson et al. | 204/148 |
| 4,400,259 | 8/1983 | Schutt | 204/196 |
| 4,442,903 | 4/1984 | Schutt et al. | 204/196 |

Primary Examiner—T. Tung
Attorney, Agent, or Firm—Robert A. Kulason; James J. O'Loughlin; Robert B. Burns

[57] ABSTRACT

Apparatus in an offshore fixed structure for monitoring the effectiveness of an under water cathodic protection system. Said system includes a guide cable, both ends of which are adjustably positioned at the structure's upper end. The cable is retained on a turning spool at the structure lower end to define parallel guide segments upon which a carriage is operably mounted. Monitoring instrumentation carried on the carriage is caused to scan the structure, thereby providing a series of readings which report on the effectiveness of the cathodic protection system.

3 Claims, 5 Drawing Figures

CATHODIC PROTECTION MONITOR SYSTEM FOR SUBMERGED STRUCTURES

BACKGROUND OF THE INVENTION

Any metallic structure which is positioned in an offshore salt water environment, will, after a period of time, be subjected to progressive corrosion and deterioration of exposed metallic parts. One way to prevent or at least deter such corrosive action is through the use of coatings such as paints and anti-corrosion systems which are capable of counteracting the deleterious effects. It has been found desirable for example to provide submerged parts of the structure with a series of sacrificial anodes. Thus, rather than the structure's metallic parts deteriorating under the cathodic effects of corrosive action, the sacrificial anodes will be progressively eaten away.

This method of corrosion control is widely practiced by the petroleum industry. Offshore drilling and producing structures frequently utilize sacrificial anodes in their prevention systems.

To maintain a desired degree of protection for the structure, these sacrificial anodes must be replaced. Normally, structures are subjected to periodic inspections usually by divers who descend with the necessary instrumentation to both test and observe the degree of protection afforded by the many sacrificial anodes. In relatively shallow water, the use of divers is found to be practical and entails minimal expenses.

The present generation of offshore structures of the type contemplated is often made for use in water depths on the order of magnitude of 1,000 feet and greater. It can be appreciated therefore that for such a structure, the use of divers to periodically descend and check the anti-corrosion system can prove to be an expensive as well as a dangerous operation.

The prior art has dealt with the subject of cathodic protection and monitoring equipment therefor. U.S. Pat. No. 4,056,446, for example, teaches the use of an instrument package which is guidably raised and lowered through an offshore structure to gather the necessary data. This arrangement, however, embodies limitations which restrict its utility.

Toward simplifying the monitoring and inspection process for relatively tall or deep offshore structures, the present invention provides means whereby the cathodic protection system can be monitored without the use of divers and by a relatively simple apparatus incorporated into the structure. Said apparatus comprises primarily a package of monitoring instruments and ancillary equipment which is capable of being raised and lowered along a guide cable as well as being horizontally adjustable to more fully scan the structure.

It is therefore an object of the invention to provide a cathodic protection monitor system for a structure positioned in an offshore body of water.

A further object is to provide a corrosion prevention monitor system which is operated and controlled from a structure's deck whereby to avoid the use of divers.

DESCRIPTION OF THE DRAWINGS

FIG. 5 is a cross-sectional view taken along line 5—5 of FIG. 4.

Referring to FIG. 1, an offshore structure 10 of the type contemplated is comprised normally of an elongated jacket which extends from the water's surface 11 down to the floor 12 of the body of water. The upper end of the jacket protrudes beyond surface 11 and is adapted to receive a working deck 13 on which the normal equipment is carried. In the instance of an offshore drilling platform, such equipment would include the usual derrick, together with facilities for storing the equipment and personnel normally utilized for drilling wells into the ocean floor.

The platform jacket is comprised primarily of a plurality of substantially vertical support legs 14 and 16. The latter are formed of steel cylindrical members which are mutually joined by a series of horizontal braces 19 as well as by intermediary bracing struts 18.

Jackets of this type are normally fabricated of welded steel tubulars, and can be coated with a surface material which will deter or substantially prevent the corrosive effect of the salt water for a limited period.

Figure 1:
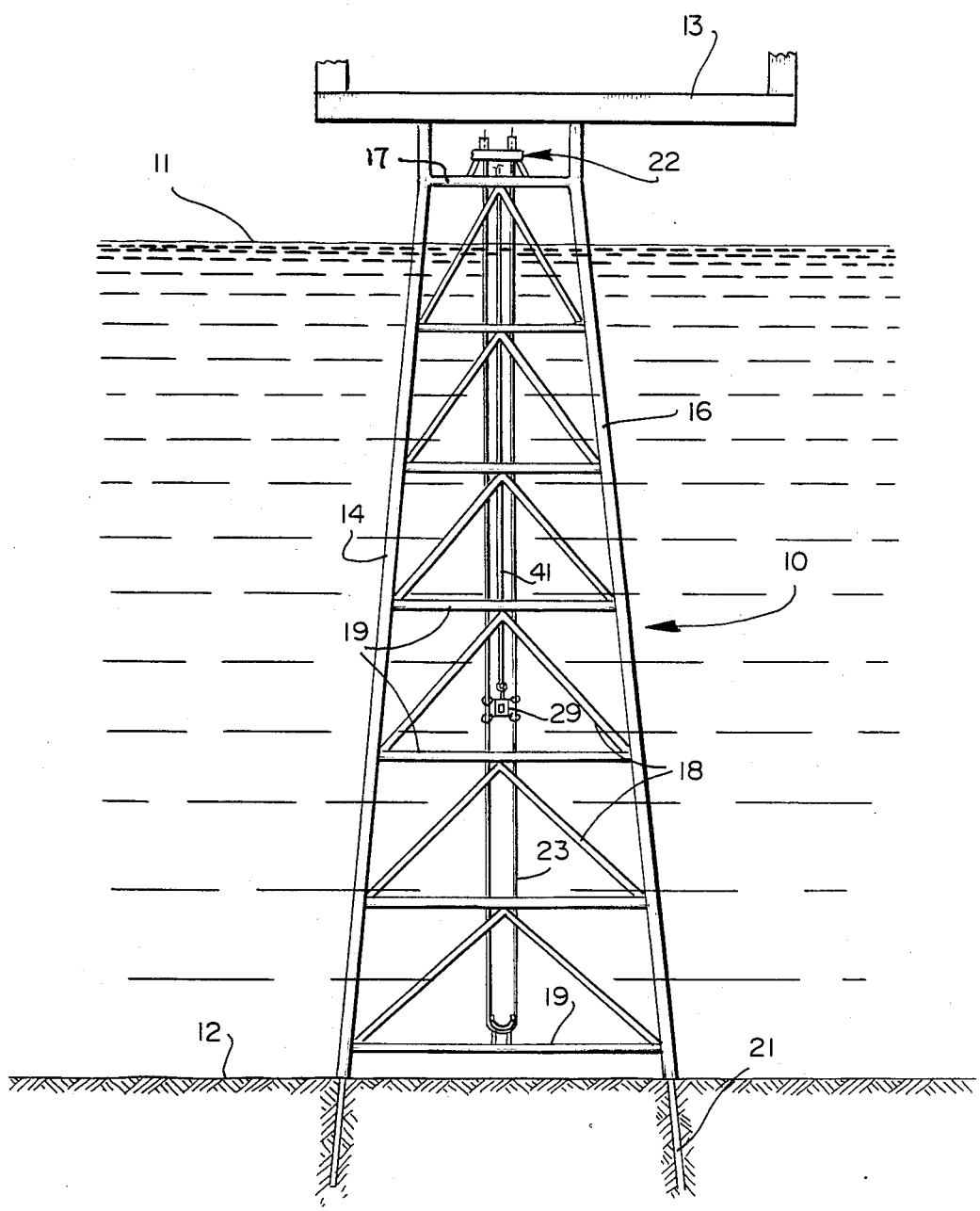
FIG. 1 is an elevation view of a marine structure of the type contemplated which embodies a cathodic protection monitor system.

The jacket shown in FIG. 1 includes a lower portion having a plurality of substantially horizontal base members 19 which extend between the respective legs 14 and 16. Following usual practice, a series of piles 21 are driven through the support legs and into the ocean floor 12 to stabilize the structure at its working site.

As mentioned herein an offshore structure 10 of this type is normally provided with an array of sacrificial anodes. The latter are disposed both vertically and horizontally along the respective metallic legs and support members to afford the desired degree of cathodic protection.

Figure 2:
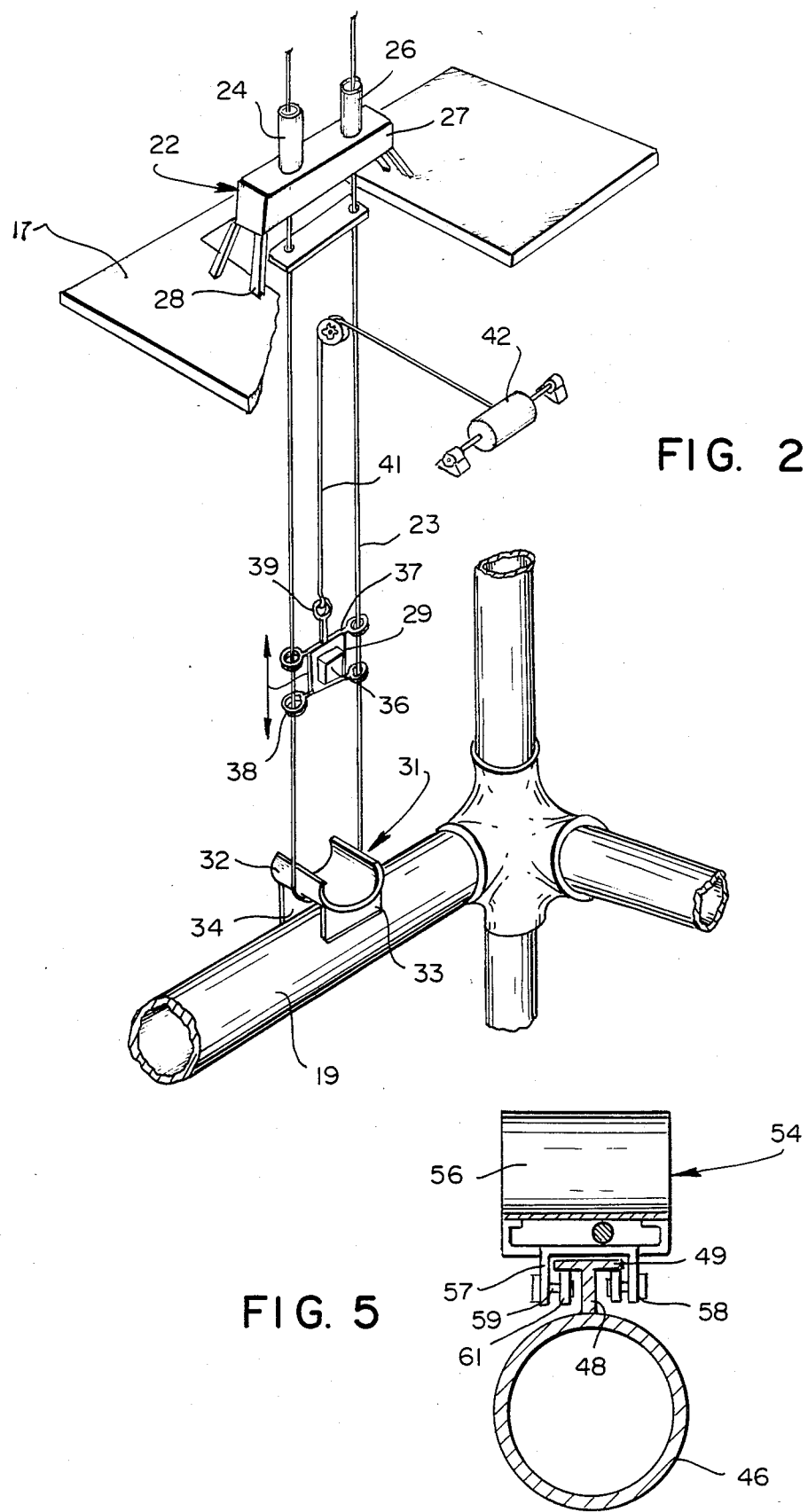
FIG. 2 is an expanded, segmentary view of the apparatus shown in FIG. 1.

Referring to FIG. 2, the present cathodic protection monitoring system is shown with portions of the structure's jacket removed. Thus, the upper end of the system includes a terminal member 22 which is supported on a horizontal member 17 or on an appropriate part of the jacket. Said terminal member is adapted to receive both ends of an elongated guide cable 23 in tensioning elements 24 and 26 in a manner that the cable ends can be held in place and appropriately adjusted.

Terminal member 22 can comprise as shown a body 27 which is supported by a series of legs 28 which in turn rest on horizontal member 17. Body 27 is provided with vertical, spaced apart openings which receive the two ends of cable 23, and conform to the width of instrument carrying carriage 29.

The lower end of the platform jacket is provided on at least one lower base member 19, with a turning spool 31. The latter comprises basically an arcuate shaped turning shoe 32 which is formed to define a curved surface along which the elongated guide cable 23 is retained.

Turning shoe 32 as shown, is formed in the present embodiment of a tubular member which has been fabricated to define a convex contact surface on which guide cable 23 is positioned.

Arcuate shoe 32 is carried on a pair of positioning brackets 33 and 34 which depend downwardly from the shoe and are fixed in place on base member 19. Normally turning spool 31 is fabricated of steel and is thus subjected to the corrosive effects herein mentioned.

However, the apparatus can be provided with coated surfaces to avoid or deter corrosion.

Elongated guide cable 23 as shown, extends from the terminal member 22, downward to the turning spool 31 having both cable ends adjustably gripped at tension members 24 and 26. The tensioned guide cable 23 thus defines a pair of spaced apart guide segments upon which instrument carrying carriage 29 can be slidably mounted.

The upper end of guide cable 23 can be adjusted such that a predetermined tension can be drawn on the guide cable 23 without exerting excessive stress on turning spool 31.

As shown, carriage 29 carrying instrumentation package 36 required for scanning and monitoring the jacket carriage 29, is slidably mounted by a plurality of outward depending arms 37 having engaging couplings 38 at the opposed ends thereof to fit on the respective guide cable segments. Coupling 38 can be removably positioned on the respective guide cable segments to permit removal of carriage 29 as required.

The upper end of the carriage 29 is provided with a connecting eye 39 which engages a take-up mechanism including an elongated take-up cable 41. One end of cable 41 is fastened to eye 39. The other end is positioned on a drum 42. The latter is controllably driven so that carriage 29 can be moved along the length of the guide cable segments during a scanning operation.

Operationally, the instrument package 36 is connected through electrical cable, not presently shown, to the appropriate instruments on deck 13. Thus, individual, or a series of readings can be taken as carriage 29 is progressively moved vertically along the guide cable segments. This monitoring can be done at periodic intervals of time, or as often as is deemed necessary to provide an accurate reading or determination of the condition of the cathodic protection system.

To extend the capability of the monitoring system, and provide a greater degree of jacket coverage, particularly for deep water jackets, the lower end of the system can be operably carried on a jacket base member. Thus, and as shown in FIGS. 3, 4, and 5, the carriage as well as the instrument package, can be horizontally adjusted relative to the jacket thereby permitting a much wider scope of data procurement.

Figure 3:
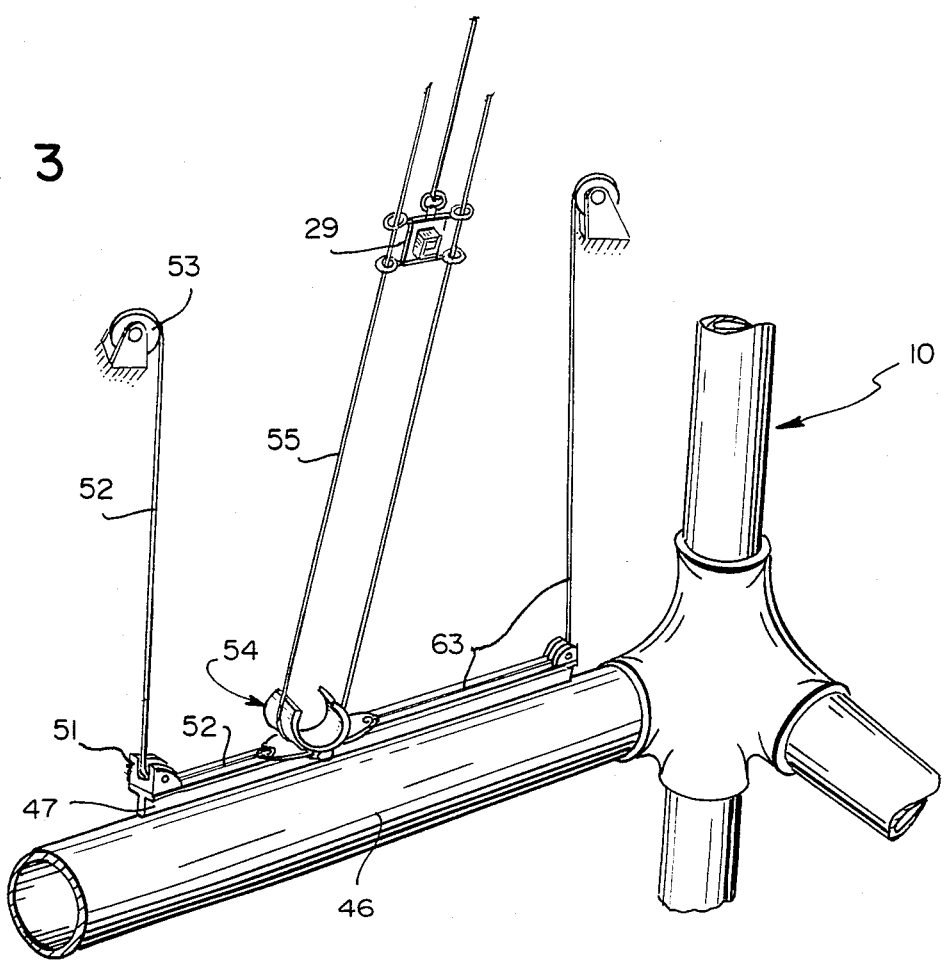
FIG. 3 is a segmentary view of an alternate form of the monitor system.
Figure 4:
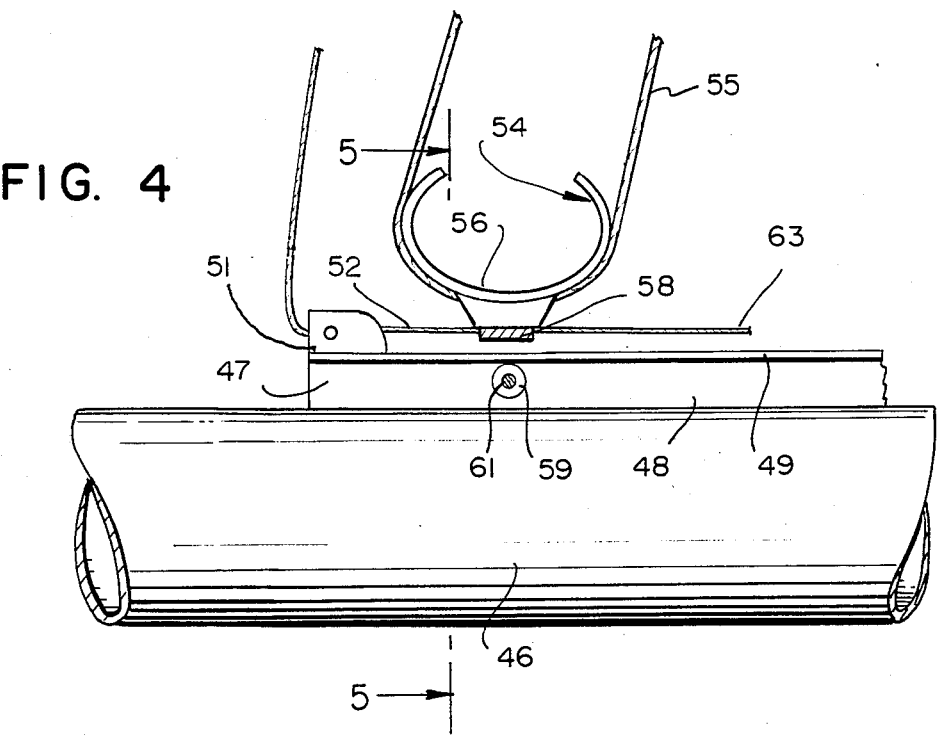
FIG. 4 is an enlarged view of the apparatus shown in FIG. 3.

Referring to FIGS. 3, 4, and 5, base member 46 is provided along its upper surface with a track 47 which extends the length of said member 46. The latter can in one embodiment take the configuration of a T-shaped element having a central vertical support 48 which is welded to the base member 46. A cross piece 49 depends from the vertical support 48 and forms a bearing surface along its underside.

Track 46 as shown is provided at opposed ends with a turning pulley 51 through which a control line 52 is threaded and guided to a control take-up 53 such as a drum or the like on the structure's working deck 13, or horizontal member 17.

The horizontally mobile turning spool 54 which engages the lower end of guide cable 55, includes an arcuate shoe 56, the outer surface of which accommodates said cable 55. The lower end of shoe 56 is provided with a downwardly extending guide bracket having spaced apart arms 57 and 58 disposed adjacent to the peripheral edges of track cross piece 49. Each bracket arm is provided with a stub shaft 59 which carries a bearing wheel 61 at the end thereof. Turning spool 54 is thereby held in position on track 46 by the respective bearing wheels in such manner that the turning spool 54 can be readily adjusted along the entire length of base member 46.

Turning spool 54 as noted is provided with oppositely positioned control lines 52 and 63 which are anchored at the turning spool bracket. They thereafter extend outwardly to the turning block 51 at each end of the track.

Preferably, control line 52 and 63 includes connecting means to engage the outer end 62 of shafts 59. Thus, the mobile turning spool 54 can be pulled to a desired position along track 46. However, the turning spool will be able to pivotally adjust about the bearing wheels, to a desired angle determined by the fixed upper end of cable 56.

Operationally, when a scan is to be made of a part of the structure's jacket, mobile turning spool 54 is displaced to a desired position by tensioning one of the positioning lines 52 while relaxing the tension on the corresponding line 63. The upper ends of guide cable 55 are thereafter adjusted by either loosening or tightening so that the turning shoe will be free to traverse the desired distance along the base member 46 guide track.

After turning spool 54 is in position, the guide cable 55 can again be made taut whereby to permit the instrument carrying carriage to be slidably positioned thereon. After the respective positioning cables 52 and 63 are tightened, the turning spool will be provisionally fixed in place to allow movement of the instrument carriage on the tensioned guide cable 55 segments.

It is seen from the respective embodiments of the invention, that the cathodic protection system on the jacket can be readily monitored at all times. Depending on the configuration of the jacket itself, the latter can be provided with as many of the monitoring systems as is deemed desirable to provide a satisfactory overall evaluation.

In either situation, in the instance of a relatively wide jacket base, the movable turning spool can be readily positioned and adjusted into place to best provide the monitoring function particularly at the jacket lower end.

It is further understood that although modifications and variations of the invention may be made without departing from the spirit and scope thereof, only such limitations should be imposed as are indicated in the appended claims.

We claim:

1. Cathodic protection monitor system for a partially submerged, elongated offshore structure 10 which includes; one or more support legs, a base member adjacent to the ocean floor, a plurality of anodes spaced vertically along the submerged portion of said structure, which afford cathodic protection to the structure, and monitoring means operable to vertically scan the structure whereby to ascertain the efficiency of said anodes in affording cathodic protection to the structure's metallic parts, which monitor system includes;

a terminal member at the structure's upper end, a turning spool depending from said base member and adapted to be moved longitudinally along the latter, a guide cable having opposed ends connected to the terminal member and engaging the turning spool to define a pair of substantially parallel cable segments, which extend between the terminal member and the turning spool, a carriage slidably mounted to the parallel cable guide segments and carrying cathodic protection monitor means thereon, and take-up means on said terminal member connected to said carriage 29 and being adjustable to regulate the vertical position of said carriage along said guide cable.

2. In the apparatus as defined in claim 1, wherein said base member includes; a track depending therefrom, and said turning spool includes a positioning bracket operably engaging said track, and traverse means engaging said turning spool being remotely operable to move said spool longitudinally along said base member track.

3. In the apparatus as defined in claim 2, wherein said traverse means includes; pulley means, and cable means having one end registered in said pulley means, the other end being at said structure upper end for moving said spool assembly longitudinally of said track.

* * * * *